(12) United States Patent
Milpied et al.

(10) Patent No.: US 8,359,091 B2
(45) Date of Patent: Jan. 22, 2013

(54) APPARATUS AND METHOD FOR DETECTING AND FILTERING ARTIFACTS BY ANALYSIS OF A CARDIAC VECTOGRAM

(75) Inventors: Paola Milpied, San Diego, CA (US); Christine Henry, Paris (FR)

(73) Assignee: Sorin CRM S.A.S., Clamart (FR)

( * ) Notice: Subject to any disclaimer, the term of this patent is extended or adjusted under 35 U.S.C. 154(b) by 142 days.

(21) Appl. No.: 13/053,843

(22) Filed: Mar. 22, 2011

(65) Prior Publication Data

US 2011/0230776 A1    Sep. 22, 2011

(30) Foreign Application Priority Data

Mar. 22, 2010 (FR) ...................... 10 52041

(51) Int. Cl.
*A61B 5/0452* (2006.01)
(52) U.S. Cl. ......... 600/516; 600/508; 600/509; 600/517
(58) Field of Classification Search .................. 600/508, 600/509, 516, 517
See application file for complete search history.

(56) References Cited

U.S. PATENT DOCUMENTS

| | | | |
|---|---|---|---|
| 6,584,351 B1 | 6/2003 | Ekwall | |
| 7,215,993 B2 | 5/2007 | Lin | |
| 7,567,835 B2 | 7/2009 | Gunderson et al. | |
| 2006/0235476 A1 | 10/2006 | Gunderson | |
| 2010/0249626 A1 | 9/2010 | El Arab et al. | |

FOREIGN PATENT DOCUMENTS

EP    2105843 A1    9/2009

OTHER PUBLICATIONS

FR, Foreign Search Report (Annexe Au Rapport De Recherche Preliminaire Relatif A La Demande De Brevet Francais No. FR1052649 FA734757), Nov. 16, 2010.
Schulte B, et al., *Inappropriate Arrhythmia Detection in Implantable Defibrillator Therapy Due to Oversensing of diaphragmatic Myopotentials*, J Interv Card Electrophysiol, 2001. 5 (4): p. 487-93.
Occhetta E, et al., *Inappropriate Implantable Cardioverter-Defibrillator Discharges Unrelated to Supraventricular Tachyarrhythmias*, Europace, 2006. 8 (10): p. 863-9.

*Primary Examiner* — Joseph Dietrich
(74) *Attorney, Agent, or Firm* — Orrick Herrington & Sutcliffe, LLP (57) ABSTRACT

Apparatus and method for detecting and filtering noise artifacts by analysis of a cardiac vectogram is disclosed. An active medical device collects electrical activity signals of a patient's heart over a series of cardiac cycles. At least two distinct temporal components ($V_{bip}$, $V_{uni}$) are obtained from at least two endocardial electrogram (EGM) signals that are collected concurrently on different respective channels from the same heart cavity. The means for analyzing and filtering of the active medical device operates by: constructing a non-temporal 2D characteristic of a vectogram (VGM) of an analyzed cardiac cycle, using a variation of one of the two distinct temporal components ($V_{uni}$) as a function of the other ($V_{bip}$); conducting a morphological analysis of the non-temporal 2D characteristic to derive at least one intrinsic descriptor parameter, including the average angle of velocity vectors of consecutive data points of the 2D characteristic, and classifying the analyzed cardiac cycle as invalid noisy cycle or as valid not noisy cycle, depending on the analysis of the descriptor parameter.

34 Claims, 6 Drawing Sheets

FIG_1

FIG_2

FIG_3

FIG_4

FIG_5

FIG_6

FIG_7A

FIG_7B

FIG_7C

FIG_7D

FIG_8A

FIG_8B

FIG_8C

FIG_8D

APPARATUS AND METHOD FOR DETECTING AND FILTERING ARTIFACTS BY ANALYSIS OF A CARDIAC VECTOGRAM

The present application claims the benefit of French application Ser. No. 10/52041 entitled "Active Medical Device Comprising Detection and Filtering Means of Artifacts by Analysis of the Cardiac Vectogram" and filed Mar. 22, 2010, which is hereby incorporated by reference in its entirety.

FIELD

The present invention relates to "active implantable medical devices" as defined by the Jun. 20, 1990 directive 90/395/CEE of the European Community Council, more specifically to devices that continuously monitor a patient's cardiac rhythm and deliver to the patient's heart, if necessary, electrical pulses for stimulation, cardiac resynchronization, cardioversion and/or defibrillation in response to a rhythm disorder detected by the devices.

It shall be noted, however, that the present invention can be implemented not only within an active implantable medical device, but also in a device located outside the patient's body, for example, in an external programmer used by a practitioner to download and analyze cardiac signals that have been collected and/or stored by an implanted medical device. The present invention can also be implemented in a home monitoring monitor, which is a special type of programmer having a fully automated operation; such a home monitoring monitor does not require intervention of a physician and serves in particular to upload data collected by an implanted medical device at regular intervals to a remote site, for remotely analyzing and monitoring the status of the patient. The present invention may also be implemented in a data server that remotely operates on the data transmitted by a home monitoring monitor.

The present invention is particularly applicable, but not limited, to apparatus for delivering to a patient's heart antitachycardia therapies for controlled application of defibrillation shocks (e.g., high energy electrical pulses designed to terminate a tachyarrhythmia), and/or therapies of high-frequency stimulation, called antitachycardia pacing ("ATP").

BACKGROUND

Active implantable medical devices are known to be sensitive to the detection of signals having a non-cardiac origin, for example, due to issues with a lead, electromagnetic interference, detection of myopotentials. These phenomena are hereinafter individually and collectively referred to under the generic term "noise". These noise phenomena are likely to generate artifacts that can lead to serious consequences, if not appropriately interpreted by a medical device, for example, by wrongly inhibiting bradycardia stimulations or resynchronization therapies, or conversely, by allowing delivery of inappropriate defibrillation shocks.

In particular, it was observed by Schulte B, et al. in *Inappropriate Arrhythmia Detection in Implantable Defibrillator Therapy Due to Oversensing of diaphragmatic Myopotentials*, J Interv Card Electrophysiol, 2001. 5 (4): p. 487-93, that among a group of 384 patients implanted with a defibrillator, 139 episodes of arrhythmia were incorrectly identified as ventricular fibrillation due to the detection of myopotentials in 33 patients (8.6%), and 32 inappropriate shocks were delivered to 11 patients (2.9%). Similarly, Occhetta E, et al. in *Inappropriate Implantable Cardioverter-Defibrillator Discharges Unrelated to Supraventricular Tachyarrhythmias*, Europace, 2006. 8 (10): p. 863-9, showed that, overall, 4% of the patients implanted with a defibrillator receive at least one inappropriate shock due to "over-detection" of extra-cardiac signals that are clinically irrelevant to supraventricular arrhythmias.

The application of a defibrillation shock to a conscious patient is generally painful and agonizing, because the applied energies are well beyond a patient's threshold of pain. In addition, the application of a defibrillation shock presents side effects on the heart rate (i.e., there is a risk of developing a secondary disorder), on the functional integrity of the myocardium, and generally on the patient's physiological balance. It is, therefore, important to deliver such shocks only when appropriate, and only when a less painful alternative therapy, such as an appropriate stimulation of the atrium, is not feasible.

Commonly used methods to filter noise signals in ventricular signals include filtering the collected signals and automatically controlling various detection parameters such as a blanking period, a sensitivity value, etc. to detect over-detections, and prohibit any inappropriate action.

U.S. Pat. No. 6,584,351 B1 proposes a method that attempts a priori to eliminate noise signals before ventricular sensing. To this end, an additional electrode, externally located from the heart, detects signals having a non-cardiac origin, which are considered as noise. These noise signals are then subtracted from the detected signals by the intracardiac electrodes. For this method to be effective, however, it requires implantation of an external electrode outside the heart, for example, on the housing of the medical device—this implicates a redesign of the mechanical and electrical structure of the medical device.

Other methods have been proposed to operate a "post-filtering" of noise signals contained in the extra-cardiac ventricular signal after they are collected. U.S. Pat. No. 7,567,835 B2 proposes to compare a ventricular marker chain produced by the defibrillator from a bipolar (nearfield) signal with an R marker chain obtained by analyzing a unipolar (farfield) signal that is simultaneously collected. The markers detected by the defibrillator from the nearfield signal, but are not detected on the farfield signal, are considered as noise. The origin of these noise signals are determined by analyzing the number and the pattern of the markers in the chains on the two channels. This technique has a disadvantage that, if an extra-cardiac signal from outside the heart is present on both channels (nearfield and farfield), it is not considered as noise, even if this phenomenon is clearly identifiable by a visual examination of the traces.

U.S. Pat. No. 7,215,993 B2, proposes to calculate a weighted average and normalized amplitude from: the amplitude of the analyzed beat, the amplitude of the preceding beat, and the amplitude of the following beat. If the average exceeds a predetermined threshold, the analyzed beat is considered valid, otherwise it is regarded as noise. However, this method is sensitive to various rhythm abnormalities occurring erratically, which may lead to both false positive and false negative results.

OBJECT AND SUMMARY

Broadly, the present invention is directed to analyzing endocardial electrogram signals (EGM signals) collected concurrently on two distinct channels and originated from a single cavity, including the ventricle, and using the EGM signals to obtain relevant parameters relating to the origin of the signals collected—whether a cardiac depolarization wave, or other artifact-generating potential.

Preferably, the two different EGM channels are respectively a unipolar signal (e.g., a distant signal collected between the housing and a distal or proximal electrode), and a bipolar signal (e.g., a signal collected between a distal electrode and a proximal electrode).

In a preferred embodiment, the EGM signals are analyzed in a two-dimensional analysis by forming a "cardiac loop" or "vectogram" (VGM), which is a non-temporal representation of the EGM signals in a two-dimensional ("2D") space. This 2D cardiac loop is typically formed by the pairs of the "unipolar channel" signal (in ordinate) and the bipolar channel signal (in abscissa)". Each beat or significant fraction of a beat is represented by its vectogram in the plane hence defined It is emphasized that this vectogram (VGM), which is obtained from the EGM signals delivered by intracardiac leads, should not be confused with the term "vectocardiogram" (VCG), which is instead obtained from signals of electrocardiogram (ECG) delivered by external electrodes placed on the patient's chest.

A related technique is described in EP 2105843 A1 and its counterpart US Patent Publication No. 2010/0249626 (both assigned to Sorin CRM S.A.S., previously known as ELA Medical), in which it is proposed to construct a representative VGM of the current cycle under the analysis in a tachycardia zone, and to compare this current VGM to one or more reference VGMs previously obtained from a patient's sinus rhythm (SR). The result of this comparison is analyzed to classify the current cycle as one the following categories: ventricular tachycardia (VT) or supraventricular tachycardia (SVT), depending on the proximity of current analyzed VGM with the reference VGMs that were previously collected and stored in the memory.

In the present invention, as discussed in more detail below, the object is to obtain one or more descriptor parameters that are representative of the intrinsic morphology of the current VGM, and not to compare the current VGM to one or more reference VGMs. The analysis of the morphological descriptor parameters help to determine whether the current beat has a cardiac origin or is noise. The intrinsic parameters include, for example, the average angle formed by consecutive velocity vectors along the path of the VGM.

It is noted that the two-dimensional (2D) analysis discussed herein should not be understood as in itself limiting. The present invention is applicable to an analysis in a higher order multidimensional space (e.g., 3D or more), by extrapolation of the teachings described herein to a situation in which the EGM signals collected from a single cavity are collected simultaneously on three or more channels.

One embodiment of the present invention is directed to an active medical device of a known type, comprising: means for collecting the electrical activity signals of a patient's heart over a series of cardiac cycles, means for producing at least two distinct temporal components from at least two endocardial EGM signals concurrently collected from a same heart cavity on different respective channels; and means for analyzing and filtering the collected endocardial EGM signals, and discriminating between an invalid noisy cardiac cycle and a valid not noisy cardiac cycle.

In a preferred embodiment, the means for analyzing and filtering the collected endocardial EGM signals includes: means for constructing a non-temporal 2D characteristic representative of the cardiac cycle, based on variations of one of said two distinct temporal components as a function of the other of said two distinct temporal components; means for analyzing morphologically a non temporal 2D characteristic of the cardiac cycle, and delivering at least one descriptor parameter of an intrinsic characteristic; and means for classifying the analyzed cardiac cycle as one of an invalid noisy cycle and a valid not noisy cycle, based on said at least one descriptor parameter.

The EGM signals concurrently collected on different respective channels preferably include a unipolar component signal collected between the housing of the medical device and a proximal or distal electrode, and a bipolar component signal collected between a proximal electrode and a distal electrode.

In one embodiment, the means for constructing the non-temporal 2D characteristic is means for constructing the 2D characteristic based upon the variation of the two distinct temporal components over a fraction or portion of the analyzed cardiac cycle, more preferably, the portion considered in a temporal window including the QRS complex of the analyzed cardiac cycle. Preferably, the descriptor parameter is a parameter representative of a velocity vector of the 2D characteristic, considered in a number of points. In a first embodiment, this descriptor parameter is based on changes in the direction of the velocity vector between given consecutive points of the 2D characteristic, especially based on the average angle formed by two consecutive velocity vectors of the 2D characteristic. The means for classifying then includes means for comparing the average angle to a first given threshold, and means for classifying the cardiac cycle as an invalid noisy cycle if the average angle is greater than the first threshold. Preferably, if the average angle is less than the first threshold, the means for classifying compares the average angle to a second given threshold below the first threshold, compares the amplitude of a depolarization peak of the analyzed cardiac cycle to a third threshold, and classifies the cardiac cycle under analysis as an invalid noisy cycle if the average angle is greater than the second threshold and the amplitude of the depolarization peak is below the third threshold, and as not noisy cycle otherwise.

In a second embodiment, the descriptor parameter is based on the variance of the norm of a velocity vector between given consecutive points of the 2D characteristic.

Advantageously, the medical device further comprises means operating in response to the classification of the cardiac cycle as invalid noisy cycle by the classifier means, for performing a function selected from among a group consisting of: erasing a marker linked to the analyzed cardiac cycle, assigning a specific marker to the analyzed cardiac cycle, inhibiting the storage of the analyzed cardiac cycle, modifying the sensitivity of the means for collecting and inhibiting the delivery of a therapy by the medical device.

BRIEF DESCRIPTION OF THE DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements and in which.

DETAILED DESCRIPTION

With reference to FIGS. 1-8, embodiments of the present invention will now be described.

As regards its software aspects, the present invention can be implemented by an appropriate programming of the controlling software of a known implantable medical device, for example, a cardiac pacemaker or a defibrillator/cardioverter, including means for collecting signals provided by endocardial leads and/or one or more implanted or non-implanted sensors. These implantable medical devices include a programmable microcontroller and/or microprocessor circuitry to receive, format, and process electrical signals collected (detected) by implanted electrodes and deliver stimulation pulses via pacing electrodes. It is possible to transmit by telemetry software that will be stored in a memory of the implantable medical devices and executed to implement the functions of the present invention. The present invention may particularly be applied to implantable medical devices such as those of the Reply, Paradym, Ovatio, Esprit or Rhapsody device families produced and marketed by Sorin CRM, Clamart France, formerly known as ELA Medical, Montrouge, France. The adaptation of these implantable medical devices to implement the functions and features of the present invention is believed to be within the abilities of a person of ordinary skill in the art, and therefore will not be described in detail.

Figure 1:
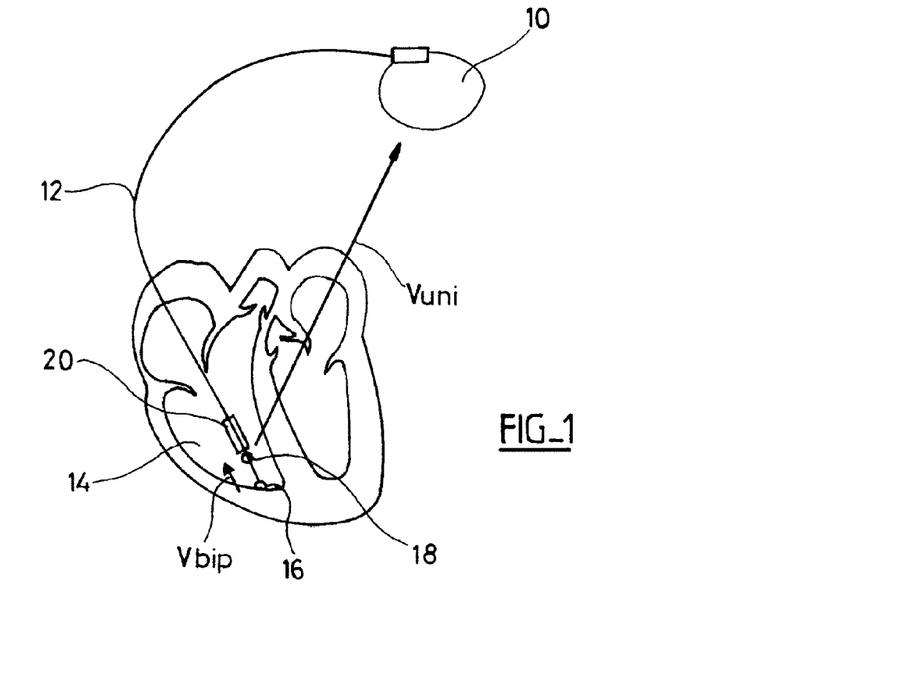
FIG. 1 is a schematic view of an implantable medical device having a bipolar lead implanted at the apex of a patient's ventricle.

FIG. 1 illustrates a "single chamber" configuration of an implantable medical device in which a generator 10 is associated with a lead 12 implanted in the right ventricle 14. The lead head has two electrodes, namely a distal electrode 16 and a proximal electrode 18, which collect a first electrogram $V_{bip}$ corresponding to the potential difference measured between the distal electrode 16 and the proximal electrode 18, and a second electrogram $V_{uni}$ measured by the potential difference between one of the electrodes, for example, the distal electrode 16 or the proximal electrode 18, and the metal housing of the generator 10.

In case when the implantable device is a defibrillator, the bipolar signal $V_{bip}$ can also be collected between the distal electrode 16 and a ventricular coil forming a defibrillation electrode 20, and the unipolar signal $V_{uni}$ can be collected between the metal housing of the generator 10 and the ventricular coil 20, or between the proximal electrode 18 and the housing 10 when the bipolar signal $V_{bip}$ is collected between the distal electrode 16 and the ventricular coil 20.

It is noted that the present invention is also applicable to the filtering of signals collected in the atrium by an appropriate electrode, or generally to the filtering of any signal collected from an electrode to detect cardiac depolarization signals, particularly multiple signals collected by a multisite device.

In general, the term "cavity" is used, and can be indifferently applied to an atrium or a ventricle of the right cavities as well as to the left cavities of a patient's heart.

According to embodiment of the present invention, an analysis is performed for each heart beat (i.e., a cardiac cycle under analysis) to distinguish between a valid non-noisy cycle that corresponds to a depolarization wave having a cardiac origin and an invalid noisy cycle that corresponds to an artifact having an extra-cardiac origin, from EGM signals that originate from a same cavity, typically the right ventricle, and are collected on two separate channels.

Figure 2:
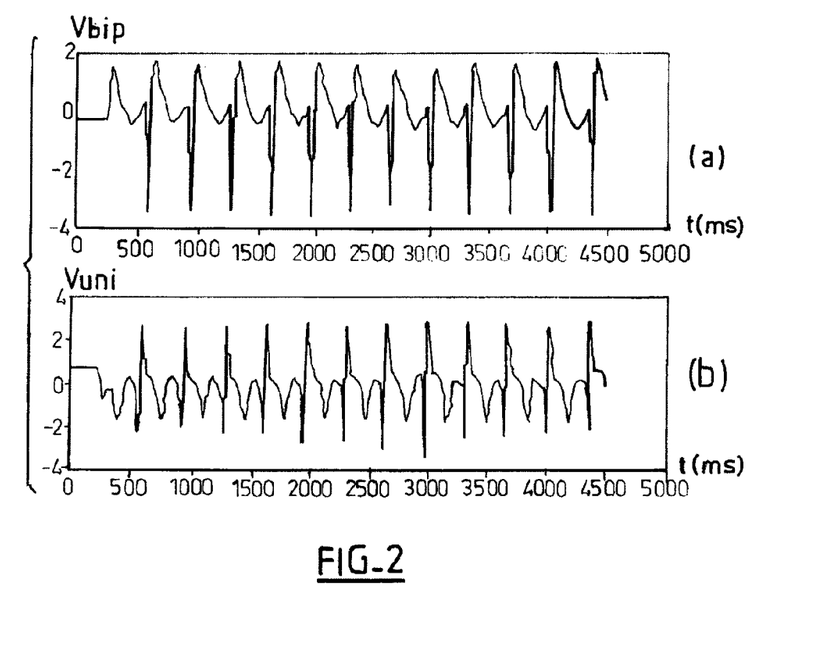
FIG. 2 illustrates exemplary EGM signals respectively collected on a ventricular bipolar channel and a ventricular unipolar channel.

FIG. 2 illustrates exemplary EGM signals $V_{bip}$ and $V_{uni}$ observed on the ventricular bipolar channel (FIG. 2a) and the ventricular unipolar channel (FIG. 2b) of the configuration as shown in FIG. 1.

It should be understood that it is not necessary to analyze the entire cardiac cycle. Rather, the analysis of a significant fraction or a portion of a cardiac cycle (typically, the portion centered on the QRS complex) is usually sufficient to discriminate between invalid noisy and valid not noisy cardiac cycles.

Figure 3:
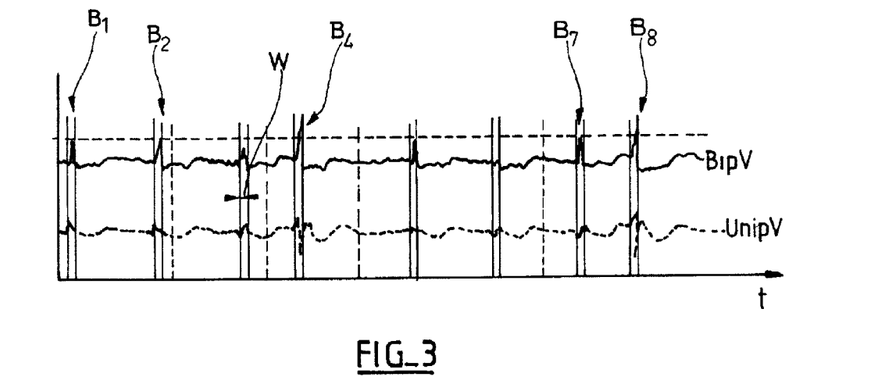
FIG. 3 illustrates the method of analysis of the EGM signals simultaneously collected on both unipolar and bipolar channels, with a window around the detected R wave on the bipolar signal, for eight successive beats.

More specifically, as shown in FIG. 3, after detecting a depolarization peak on the bipolar signal $V_{bip}$ that corresponds to a detected R wave, the corresponding beat is isolated by a fixed window W of a few tens of milliseconds that is centered on the detected depolarization peak. For example, a suitable window has a width W of 80 ms, corresponding to 80 data points for an algorithm using a sampling frequency of 1 KHz.

The successive beats B1 . . . B8 are simultaneously recorded on the ventricular bipolar channel ($V_{bip}$) and on the ventricular unipolar channel ($V_{uni}$), and the portion of each of these beats contained within the window W is then represented as a characteristic curve in a 2D plane formed by the bipolar channel $V_{bip}$ in abscissa and the unipolar channel $V_{uni}$ in ordinate. This characteristic or feature is referred to as either a "cardiac loop" or a "vectogram" ("VGM"). This VGM represents a complete heart beat in a non-temporal 2D space. As noted above, the vectogram ("VGM") is to be distinguished from a vectocardiogram ("VCG"), which is obtained from external ECG electrocardiogram signals, and not from EGM signals that are intracardiac cardiac signals.

Figure 4:
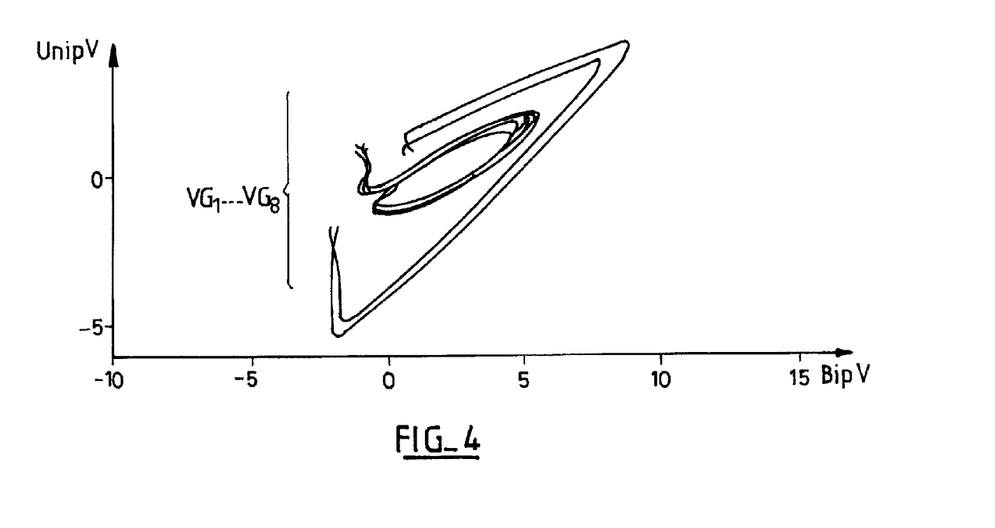
FIG. 4 illustrates exemplary vectograms collected by combining the two signals of FIG. 3, for various successive beats.

The corresponding VGM $V_1 \ldots V_8$ are shown in FIG. 4. It is noted that the VGM may not be in a form a closed loop but may represent only a portion of a complete cardiac cycle, including a region of the QRS complex and some leading and following signals isolated inside the window W.

It shall be noted that the EGM of FIG. 3 and the VGM of FIG. 4 correspond to a sampling frequency of 1 KHz, representing about 80 sampling points for each VGM in each analyzed cardiac cycle. The present technique is effective, however, even with a lower sampling frequency, e.g., 128 Hz, giving only about 10 sampling points for a VGM, as in the case of the various cycles used in the analysis algorithms of FIG. 5 and FIG. 6.

The present invention operates, essentially, for each cycle to discriminate between invalid noisy cycles and valid not noisy cycles by analyzing the corresponding VGM. In one embodiment, the analysis is performed as illustrated by the exemplary flowchart of FIG. 5. The analysis starts with the windowing as explained above in reference to FIG. 3, by sensing the R wave on the bipolar channel (step 20), searching for the depolarization peak of the R wave (step 22), and selecting a part of the signal that falls within a window of 80 ms centered on or about the peak of the R wave (step 24).

At least one descriptor parameter related to the intrinsic morphology of the current VGM is obtained. The analysis of this morphological descriptor parameter determines whether the current cardiac cycle under analysis has a cardiac origin, or is noise.

In one embodiment of the present invention, this descriptor parameter is the average angle formed by the consecutive velocity vectors along the path of the VGM, i.e., the vectors appearing at the data points at which the signal samples are collected based on the sampling rate. The choice of this descriptor parameter is based on the assumption that for a non-noisy cardiac complex (i.e., signal whose origin is a cardiac depolarization wave), two consecutive velocity vectors do not change in direction by too much. Indeed, in case of a non-noisy heartbeat, there exists a correlation between the detected signals on both channels that ensures steady VGM progression. Conversely, in case of a noisy cycle (i.e., an artifact having an extra-cardiac origin), the VGM progresses erratically, so that two consecutive velocity vectors are directed in different, and sometimes in opposite directions.

The choice of the velocity vectors is not limiting, however, and other descriptor parameters can be used—either as an alternative or in complement—to discriminate between cardiac beats and noise. For example, the variance of the average angle between consecutive velocity vectors, or more generally, any descriptor that is representative of a steady progression of the consecutive points of the VGM, may be used.

Figure 5:
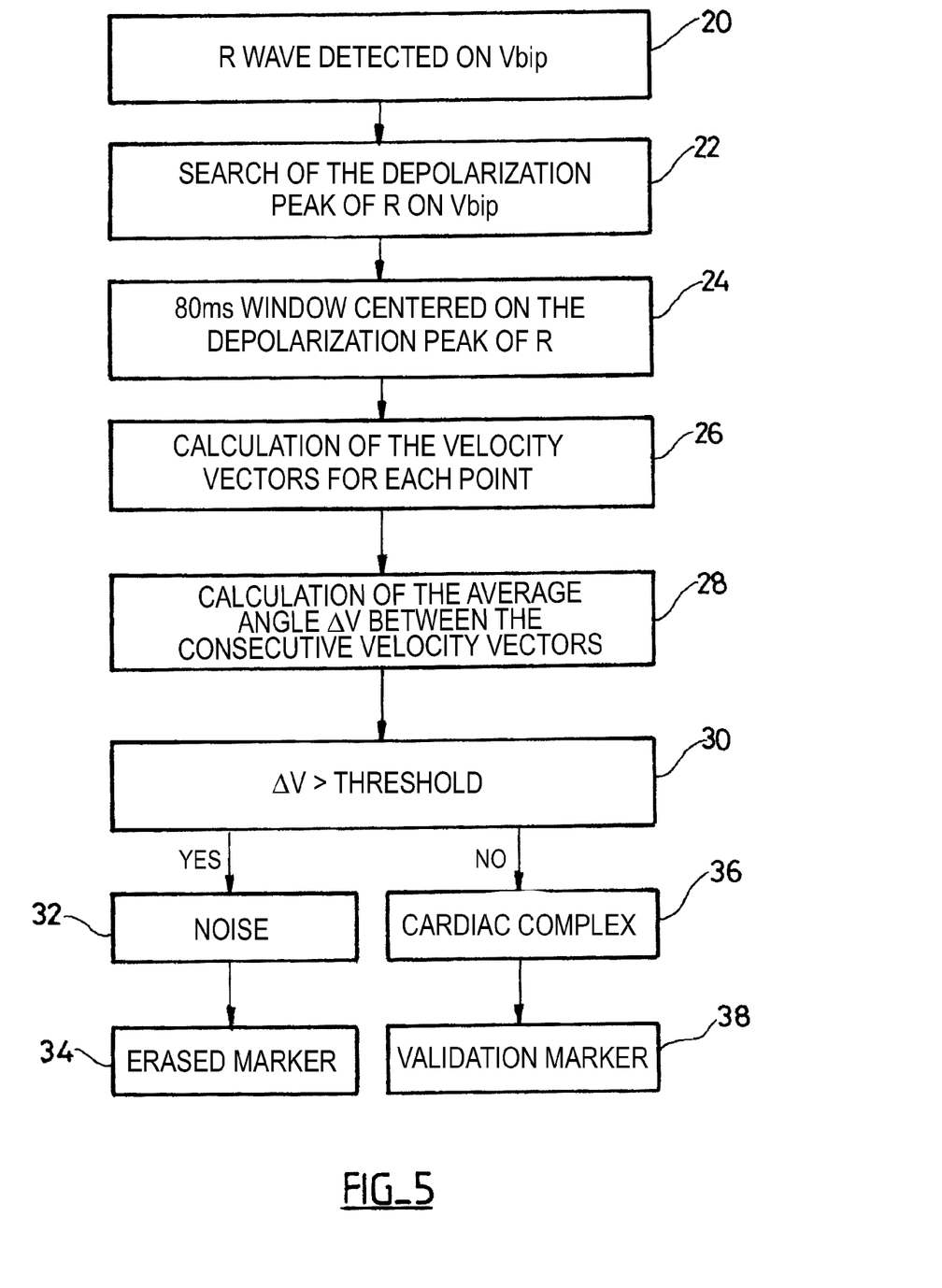
FIG. 5 is a flow chart describing a first embodiment of a filtering algorithm of the present invention.

The velocity vector $\vec{v}(t)$ is calculated (step 26) at each point t from a digital filter that approximates the first derivatives $V'_{bip}(t)$ and $V'_{uni}(t)$ (on 4 points for a sampling frequency of 1 KHz and on 2 points for a sampling frequency of 128 Hz):

$$V'_{bip}(t)=(V_{bip}(t+2)+2V_{bip}(t+1)-2V_{bip}(t-1)-V_{bip}(t-2))/8$$

$$V'_{uni}(t)=(V_{uni}(t+2)+2V_{uni}(t+1)-2V_{uni}(t-1)-V_{uni}(t-2))/8$$

$$\vec{v}(t)=(V'_{bip}(t),V'_{uni}(t))$$

To calculate (step 28) the descriptor ΔV that corresponds to the average angle between two consecutive velocity vectors, one can advantageously use the cosine of each angle. Indeed, with unit vectors, the cosine of the angle between two vectors (a, b) and (c, d) is equal to the scalar product a·c+b·d of these vectors, which greatly simplifies the calculation of the descriptor ΔV, and is expressed by:

$$\Delta V=|\text{mean}(\cos(\text{angle}(\vec{v}(1),\vec{v}(2))), \cos(\text{angle}(\vec{v}(2),\vec{v}(3))),\ldots,\cos(\text{angle}(\vec{v}(n-1),\vec{v}(n)))-1|.$$

The descriptor ΔV takes values between 0 (for an angle of 0°) and 2 (for an angle of 180°).

According to one embodiment, the descriptor ΔV hence calculated is compared to a threshold, e.g., a threshold equal to 0.9 (step 30):
  if ΔV is greater than the threshold, it is determined that the VGM does not represent a cardiac complex, the cycle is considered as an invalid noisy cycle (step 32), and it is preferably erased from the chain of markers (step 34);
  if ΔV is less than or equal to the threshold, the cycle is considered a valid, not noisy cycle, having cardiac beats of a cardiac origin (step 36), and the corresponding marker is validated (step 38).

Figure 6:
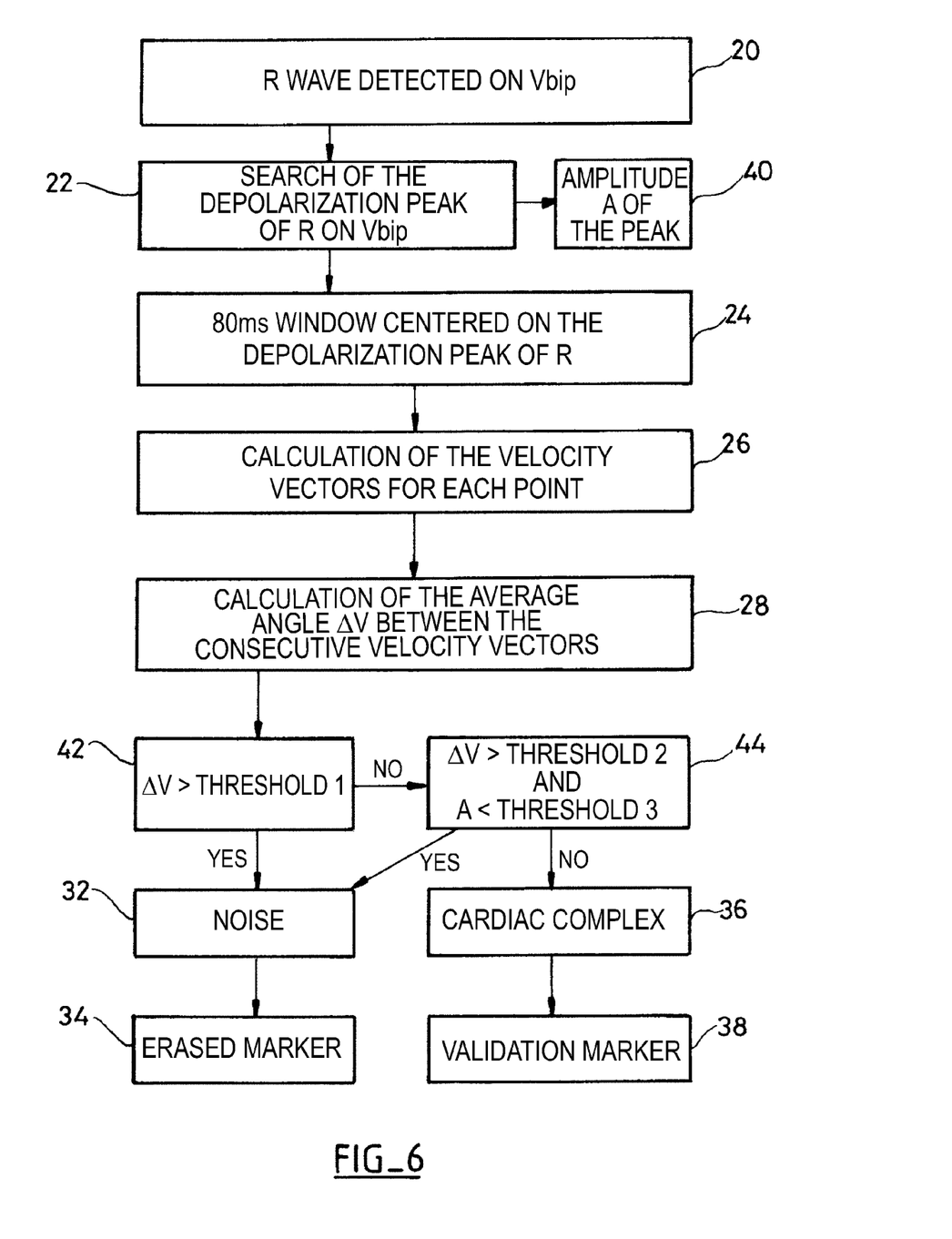
FIG. 6 is a flow chart describing a second embodiment of a filtering algorithm of the present invention.
Figure 7A:
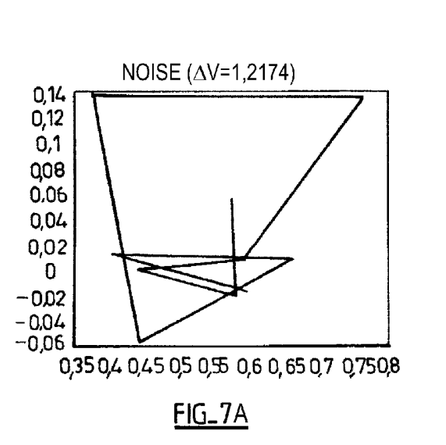
FIG. 7 illustrates various examples of vectograms analyzed by an embodiment of the present invention and classified as noise.
Figure 7B:
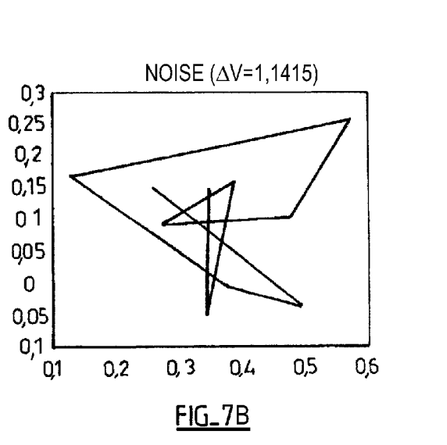
Figure 7C:
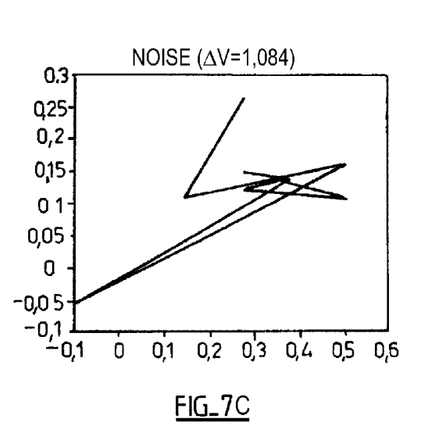
Figure 7D:
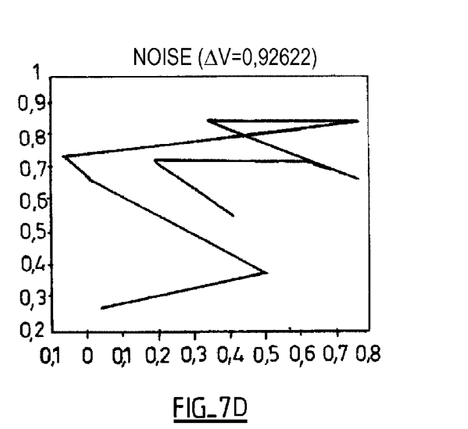
Figure 8A:
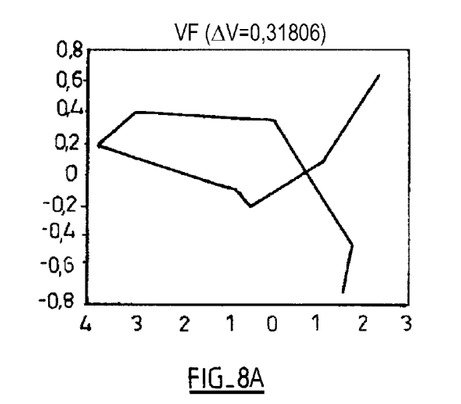
FIG. 8 illustrates various examples of vectograms analyzed by an embodiment of the present invention and classified as valid cardiac signals of ventricular fibrillation.
Figure 8B:
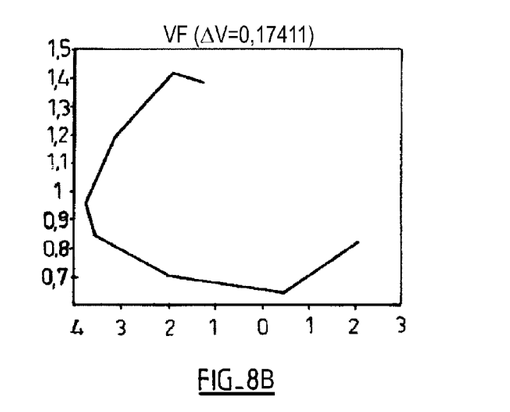
Figure 8C:
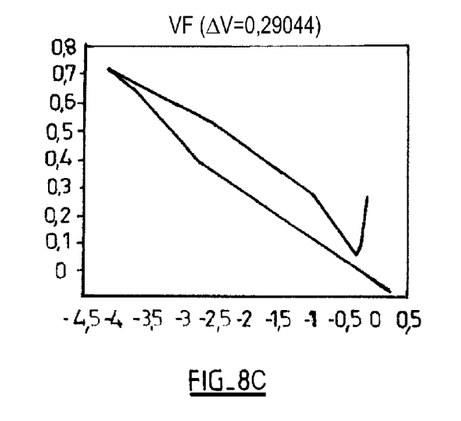
Figure 8D:
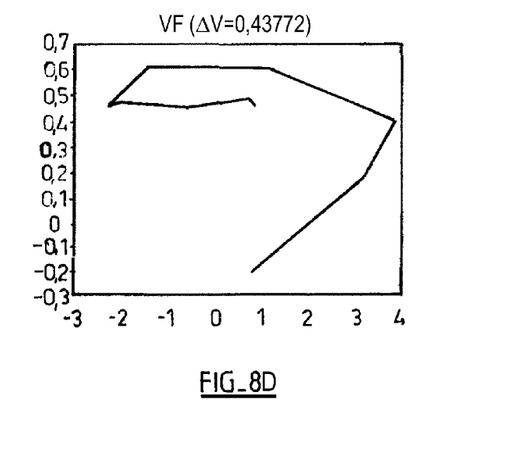

The flowchart in FIG. 6 illustrates a second embodiment of the present invention that is a variant of the first embodiment shown in FIG. 5. This algorithm avoids or reduces occurrence of under-detection especially in case of ventricular fibrillation. To this end, after calculating the descriptor ΔV (steps 20-28, being identical to those same steps 20-28 of FIG. 5), ΔV is compared to two different thresholds, one of which depends on the amplitude A of the depolarization peak, stored (step 40) during the search for this peak on the signal of the bipolar channel (step 22).

As in the previous case, the descriptor ΔV is compared to a first threshold Threshold1 independent of the amplitude A of the depolarization peak, but this threshold Threshold1 is set to be greater than the threshold of FIG. 5, e.g., 1. If ΔV is greater than Threshold1 (step 42), as in the previous case, the cycle is considered an invalid noisy cycle (steps 32 and 34).

Otherwise, ΔV is compared to a second threshold Threshold2, which is less than Threshold1, for example, Threshold2=0.8, and this second threshold is only applied if the amplitude A of the depolarization peak is sufficiently low (e.g., amplitude A<Threshold3=3 mV). If these two conditions are verified, the corresponding cardiac cycle is considered to be an invalid noisy cycle (steps 32-34), otherwise, the cycle is considered a valid non-noisy cycle, representative of a cardiac complex (steps 36-38).

FIG. 7 and FIG. 8 illustrate various examples of vectograms analyzed by the technique of the present invention and respectively classified as noise and valid signals of ventricular fibrillation. The calculated values of the descriptor parameter ΔV are also indicated in these figures. FIG. 7 illustrates VGMs of noisy cycles of non-cardiac origin in which several sharp changes of direction are shown that represent typical noise signals of non-cardiac origin. In contrast, FIG. 8 illustrates VGMs of not noisy cycles of cardiac origin in which the transitions are much more gradual for all or almost all sampling points in the VGM.

Although one or two locally abrupt variations can be seen in FIG. 8, unlike the noise signals of FIG. 7, they are still low in count, resulting in a relatively low value for the mean angle, thus reflected in the value of the descriptor ΔV.

Various actions are undertaken, preferably as implemented in the controlling software of the implantable medical device, following the classification between valid cycles and invalid cycles, including one or more of the followings:
  erasing of the markers corresponding to invalid noisy cycles;
  possible modification of the sensitivity of the detection circuits;
  inhibition of a therapy;
  modification of the episodes identification label; and
  erasing of the memory of the episodes of noise, especially for non-sustained episodes.

If the defibrillator already implements a discrimination algorithm of VT/SVT arrhythmias by the technique described in EP 2105843 A1 and its counterpart US Patent Publication 2010/0249626, the VGM is constituted and analyzed, and velocity vectors are calculated, so that the noise removal technique according to the present invention can be implemented with a very low or no additional cost using the existing software resources.

One skilled in the art will appreciate that the present invention can be implemented by other methods and processes than the embodiments disclosed herein, which are provided for purposes of illustration but not of limitation.

The invention claimed is:

1. An active medical device (10, 12), for collecting electrical activity signals of a patient's heart over a series of cardiac cycles, comprising:
  means for collecting concurrently at least two endocardial electrogram (EGM) signals, the at least two EGM signals being collected on different respective channels and derived from a single cavity of the patient's heart;
  means for producing at least two distinct temporal components from said at least two EGM signals; and
  means for analyzing and filtering said at least two EGM signals for an analyzed cardiac cycle of the series of cardiac cycles, wherein the means for analyzing and filtering comprises:
means for constructing a two-dimensional (2D) non-temporal characteristic (VGM) representative of said analyzed cardiac cycle, as a function of one of said at least two temporal components with respect to the other of said at least two temporal components;
means for analyzing morphologically the 2D non-temporal characteristic (VGM) and delivering at least one descriptor parameter of said 2D non-temporal characteristic (VGM); and
means for classifying said analyzed cardiac cycle as one of an invalid noisy cycle and a valid non-noisy cycle, based on said at least one descriptor parameter.

2. The device of claim 1, wherein said at least two EGM signals on different respective channels comprise:
a unipolar component signal ($V_{uni}$) collected between a housing and a proximal or distal electrode of the active medical device; and
a bipolar component signal ($V_{bip}$) collected between a proximal electrode and a distal electrode of the active medical device.

3. The device of claim 1, wherein the means for constructing the 2D non-temporal characteristic comprises means for constructing the 2D characteristic from variations of said at least two distinct temporal components over a portion of the analyzed cardiac cycle, said portion corresponding to a temporal window including a QRS complex of said analyzed cardiac cycle.

4. The device of claim 1, wherein said 2D non-temporal characteristic comprises a first plurality of data points and said at least one descriptor parameter is a parametric function of a velocity vector of the 2D non-temporal characteristic at a second plurality of said data points.

5. The device of claim 4, wherein said velocity vector has a direction at each data point and said at least one descriptor parameter is based on variations in the direction of the velocity vector between consecutive data points of the given 2D non-temporal characteristic.

6. The device of claim 5, wherein said at least one descriptor parameter is based on the average angle formed by two consecutive velocity vectors of the 2D non-temporal characteristic.

7. The device of claim 6, wherein the means for classifying comprises:
means for comparing the average angle to a first threshold; and
means for classifying the analyzed cardiac cycle as an invalid noisy cycle if the average angle is greater than the first threshold.

8. The device of claim 7, wherein the means for classifying comprises:
means for, if the average angle is less than the first threshold, comparing the average angle to a second threshold, the second threshold being less than the first threshold, and comparing the amplitude of a depolarization peak of the analyzed cardiac cycle to a third threshold; and
means for classifying the analyzed cardiac cycle as an invalid noisy cycle if the average angle is greater than the second threshold and the amplitude of the depolarization peak is less than the third threshold, and otherwise as not noisy cycle.

9. The device of claim 4, wherein said at least one descriptor parameter is based on variance of the norm of the velocity vector between consecutive data points of the given 2D non-temporal characteristic.

10. The device of claim 1, further comprising means for erasing a marker linked to the analyzed cardiac cycle, wherein the means for erasing a marker operates in response to the invalid noisy cycle.

11. The device of claim 1, further comprising means for assigning a specific marker to the analyzed cardiac cycle, wherein the means for assigning a specific marker operates in response to the invalid noisy cycle.

12. The device of claim 1, further comprising means for inhibiting storage of the analyzed cardiac cycle, wherein the means for inhibiting storage operates in response to the invalid noisy cycle.

13. The device of claim 1, further comprising means for changing sensitivity of the collecting means, wherein the means for changing sensitivity operates in response to the invalid noisy cycle.

14. The device of claim 1, further comprising means for inhibiting the delivery of a therapy by the device, wherein the means for inhibiting operates in response to the invalid noisy cycle.

15. An active medical device (10, 12) for collecting electrical activity signals of a patient's heart over a series of cardiac cycles, comprising:
means for collecting concurrently a first endocardial electrogram (EGM) signal and a second endocardial EGM signal, said first and second EGM signals being collected on different respective channels and derived from a single cavity of the patient's heart;
means for producing a first temporal component and a second temporal component from said first and second EGM signals, said first and second temporal components being distinct from each other; and
means for analyzing and filtering said first and second EGM signals, for an analyzed cardiac cycle of the series of cardiac cycles,
wherein the means for analyzing and filtering comprises:
means for constructing a two-dimensional (2D) non-temporal characteristic (VGM) representative of said analyzed cardiac cycle, using a plurality of pairs of said first and second temporal components;
means for analyzing morphologically the 2D non-temporal characteristic (VGM) and delivering a descriptor parameter of said 2D non-temporal characteristic (VGM); and
means for classifying said analyzed cardiac cycle as one of an invalid noisy cycle and a valid non-noisy cycle, based on said delivered descriptor parameter.

16. The device of claim 15, wherein said first and second EGM signals on different respective channels comprise:
a unipolar component signal ($V_{uni}$) collected between a housing and a proximal or distal electrode, associated with said active medical device; and
a bipolar component signal ($V_{bip}$) collected between a proximal electrode and a distal electrode associated with said active medical device.

17. The device of claim 15, wherein the means for constructing the 2D non-temporal characteristic comprises means for constructing the 2D non-temporal characteristic from variations of said first and second temporal components over a portion of the analyzed cardiac cycle, said portion corresponding to a temporal window including a QRS complex of said analyzed cardiac cycle.

18. The device of claim 15, wherein said 2D non-temporal characteristic comprises a first plurality of data points and said descriptor parameter is a parametric function of a velocity vector of the 2D non-temporal characteristic at a second plurality of said data points.

19. The device of claim 18, wherein said velocity vector has a direction at each data point and said descriptor parameter is based on variations in the direction of the velocity vector between consecutive data points of the given 2D non-temporal characteristic.

20. The device of claim 19, wherein said descriptor parameter is based on the average angle formed by two consecutive velocity vectors of the 2D non-temporal characteristic.

21. The device of claim 20, wherein the means for classifying comprise:
means for comparing the average angle to a first threshold; and
means for classifying the analyzed cardiac cycle as an invalid noisy cycle if the average angle is greater than the first threshold.

22. The device of claim 21, wherein the means for classifying comprises:
means for, if the average angle is less than the first threshold, comparing the average angle to a second threshold, the second threshold being less than the first threshold, and comparing the amplitude of a depolarization peak of the analyzed cardiac cycle to a third threshold; and
means for classifying the analyzed cardiac cycle as an invalid noisy cycle if the average angle is greater than the second threshold and the amplitude of the depolarization peak is less than the third threshold, and otherwise as not noisy cycle.

23. The device of claim 18, wherein said descriptor parameter is based on variance of the norm of the velocity vector between consecutive data points of the given 2D non-temporal characteristic.

24. The device of claim 15, further comprising means for performing a device function in response to the invalid noisy cycle, the means for performing the device function selected from among a group consisting of:
means for erasing a marker linked to the analyzed cardiac cycle;
means for assigning a specific marker to the analyzed cardiac cycle;
means for inhibiting the storage of the analyzed cardiac cycle;
means for changing sensitivity of the means for collecting; and
means for inhibiting delivery of a therapy by the device.

25. A method of analyzing electrical activity signals of a patient's heart over a series of cardiac cycles, the method comprising:
collecting concurrently at least two endocardial electrogram (EGM) signals on different respective channels, the at least two EGM signals being derived from a single cavity of the patient's heart;
producing at least two distinct temporal components from said at least two EGM signals;
analyzing and filtering said at least two EGM signals for an analyzed cardiac cycle of the series of cardiac cycles;
constructing a two-dimensional (2D) non-temporal characteristic (VGM) representative of said analyzed cardiac cycle, as a function of one of said at least two temporal components with respect to the other of said at least two temporal components;
analyzing morphologically the 2D non-temporal characteristic (VGM) and delivering at least one descriptor parameter of said 2D non-temporal characteristic (VGM); and
classifying said analyzed cardiac cycle as one of an invalid noisy cycle and a valid non-noisy cycle, based on said at least one descriptor parameter.

26. The method of claim 25, wherein said at least two EGM signals on different respective channels comprise:
a unipolar component signal ($V_{uni}$) collected between a housing and a proximal or distal electrode of an active medical device; and
a bipolar component signal ($V_{bip}$) collected between a proximal electrode and a distal electrode of the active medical device.

27. The method of claim 25 further comprising constructing the 2D characteristic from variations of said at least two distinct temporal components over a portion of the analyzed cardiac cycle, said portion corresponding to a temporal window including a QRS complex of said analyzed cardiac cycle.

28. The method of claim 25, wherein said 2D non-temporal characteristic comprises a first plurality of data points and said at least one descriptor parameter is a parametric function of a velocity vector of the 2D non-temporal characteristic at a second plurality of said data points.

29. The method of claim 28, wherein said velocity vector has a direction at each data point and said at least one descriptor parameter is based on variations in the direction of the velocity vector between consecutive data points of the given 2D non-temporal characteristic.

30. The method of claim 29, wherein said at least one descriptor parameter is based on the average angle formed by two consecutive velocity vectors of the 2D non-temporal characteristic.

31. The method of claim 30 further comprising:
comparing the average angle to a first threshold; and
classifying the analyzed cardiac cycle as an invalid noisy cycle if the average angle is greater than the first threshold.

32. The method of claim 31 further comprising:
comparing the average angle to a second threshold if the average angle is less than the first threshold, the second threshold being less than the first threshold;
comparing the amplitude of a depolarization peak of the analyzed cardiac cycle to a third threshold; and
classifying the analyzed cardiac cycle as an invalid noisy cycle if the average angle is greater than the second threshold and the amplitude of the depolarization peak is less than the third threshold, and otherwise as not noisy cycle.

33. The method of claim 28, wherein said at least one descriptor parameter is based on variance of the norm of the velocity vector between consecutive data points of the given 2D non-temporal characteristic.

34. The method of claim 25 further comprising performing a device function of an active medical device in response to the invalid noisy cycle, the device function selected from among a group consisting of:
erasing a marker linked to the analyzed cardiac cycle;
assigning a specific marker to the analyzed cardiac cycle;
inhibiting storage of the analyzed cardiac cycle;
changing the sensitivity of the collecting the EGM signals; and
inhibiting the delivery of a therapy by the active medical device.

* * * * *